United States Patent [19]

Emmons

[11] 4,259,073
[45] Mar. 31, 1981

[54] EXTRA CORONAL ATTACHMENT

[76] Inventor: James D. Emmons, 15 E. Franklin, Bellbrook, Ohio 45305

[21] Appl. No.: 920,286

[22] Filed: Jun. 29, 1978

Related U.S. Application Data

[63] Continuation-in-part of Ser. No. 760,080, Jan. 17, 1977, abandoned.

[51] Int. Cl.³ .............................................. A61C 00/00
[52] U.S. Cl. .................................. 433/177; 433/219; 433/183
[58] Field of Search ...................... 32/5, 6, 7; 433/177, 433/219, 183

[56] References Cited

U.S. PATENT DOCUMENTS

| 1,140,537 | 5/1915 | Skinner | 32/5 |
| 2,609,605 | 9/1952 | Dillon | 32/5 |
| 3,535,787 | 10/1970 | Korfe | 32/5 |

FOREIGN PATENT DOCUMENTS

| 177877 | 5/1951 | Austria | 433/183 |

*Primary Examiner*—Robert Peshock
*Attorney, Agent, or Firm*—Biebel, French & Nauman

[57] ABSTRACT

An extra coronal attachment (denture) comprises a cylindrical anchor member formed as part of a crown to be attached to a natural tooth, including a cylindrical anchor surface having a predetermined angular relation to the jaw. A replaceable clip is included in a socket formed in the partial denture, and has a semi-cylindrical cavity constructed to fit closely over the anchor surface, having sufficient flexibility to be forced onto and off of the anchor surface. The anchor surface preferably is a groove formed in the cylinder, and the clip is proportioned to snap into the groove. Also, the clip is dimensioned so as to allow its side walls to flex during attachment and removal of the denture. The denture, when in place, has essentially stress free or stress isolated connections to the crowns. The clip may be constructed as an integral part of the denture, but preferably is a replaceable piece snapped into a socket integrated into a partial denture. There is also disclosed a process of constructing extra coronal attachments for partial dentures, incorporating the anchor members and clips.

3 Claims, 14 Drawing Figures

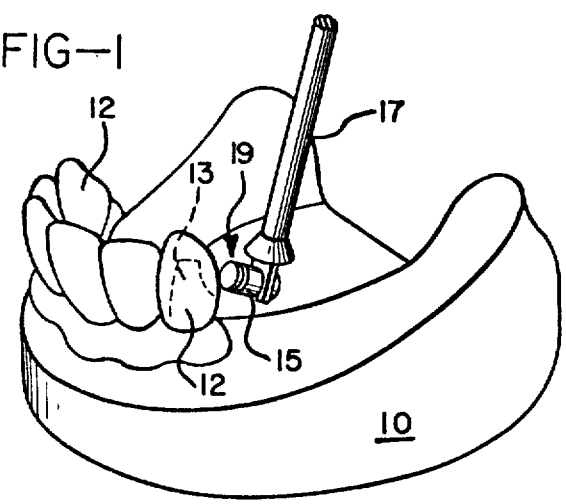
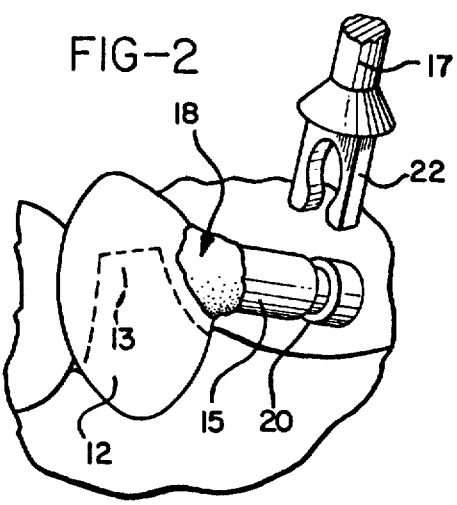
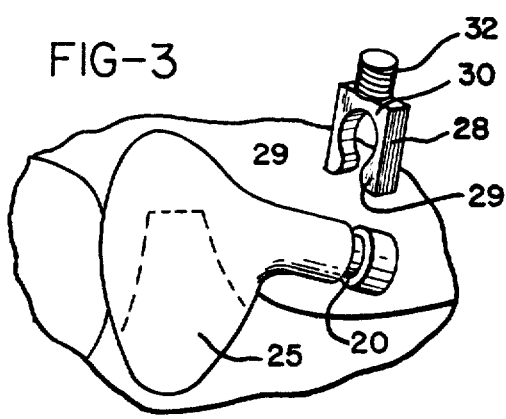
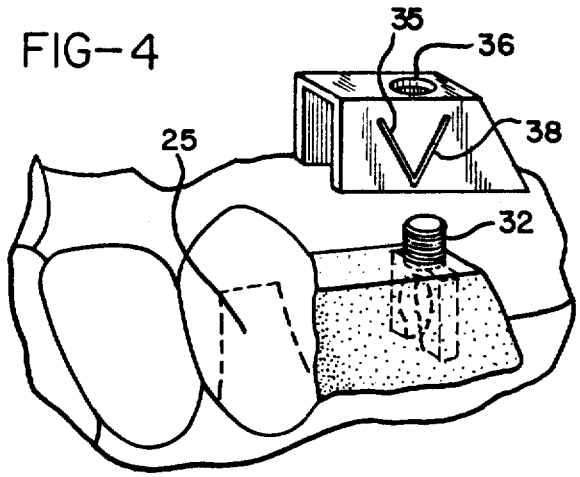
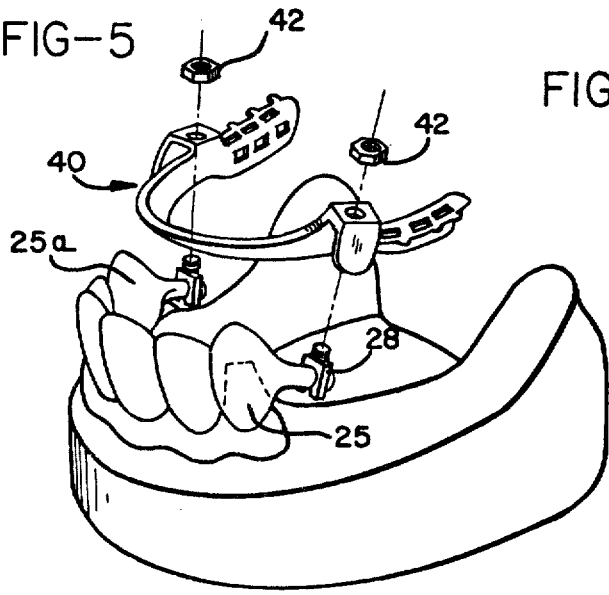
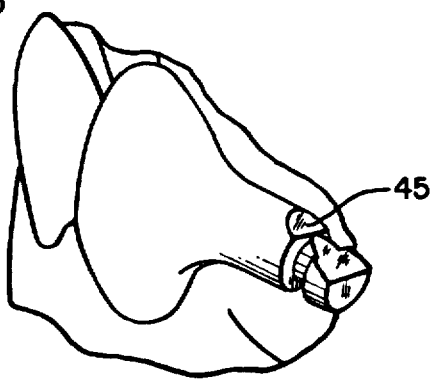
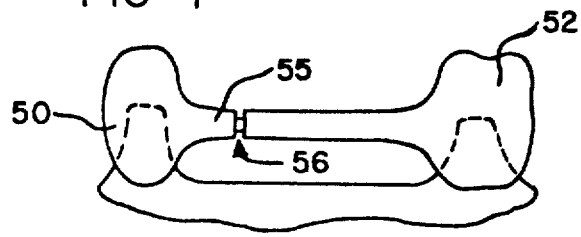

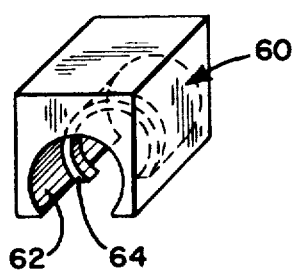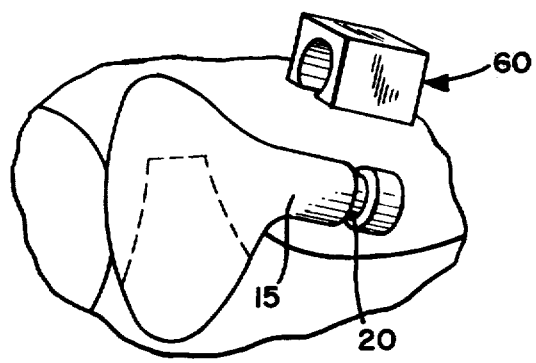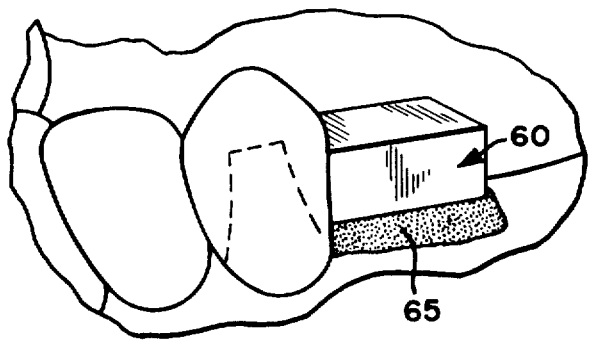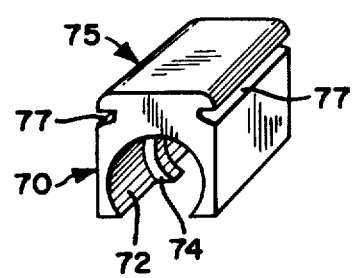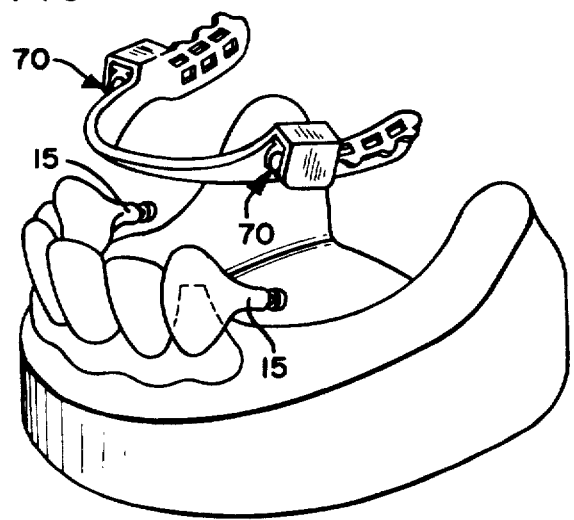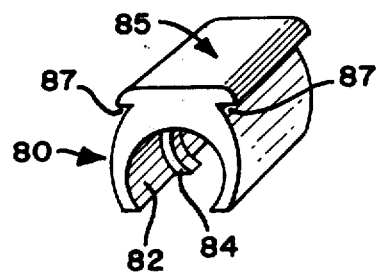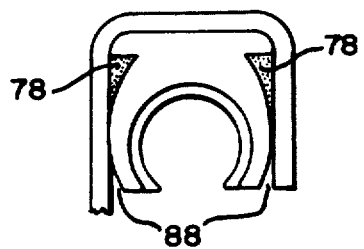

EXTRA CORONAL ATTACHMENT

CROSS-REFERENCE TO RELATED APPLICATION

This application is a continuation-in-part of application Ser. No. 760,080 filed Jan. 17, 1977 and now abandoned.

BACKGROUND OF THE INVENTION

This invention relates to the construction and attachment of partial artificial dentures, and particularly to the structure of such attachments and the process of manufacturing them.

The most common form of partial artificial denture, sometimes referred to as partial plate, involves the use of wire-like clasps or the like which engage around one or more of the wearers remaining teeth, and which hold the denture in position. Considerable difficulty is experienced with such arrangements breaking, bending and losing their holding force, or otherwise changing the predetermined position of the partial denture to the point where it is uncomfortable and possibly irritates the wearer, and/or is subjected to unusual stresses which results in breakage, either of the attachment parts or in some cases the partial denture itself. Furthermore, existing attachment arrangements are somewhat limited in their application, and particularly have not been found suitable for partial dentures which might be required on only one side of the patient's mouth.

Furthermore, existing retention arrangements involve silver solder or similar connections which tend to break, and which are particularly sensitive to flexing which may occur during usage of the denture, yet it is desirable that the attachment of the denture to the existing teeth be somewhat flexible, so that stresses are not transferred to the anchoring existing teeth, thereby compounding the dental problem of the wearer.

Various attachment devices of this nature are disclosed in U.S. Pat. Nos. 1,299,364; 1,367,885; 1,423,288; 1,696,422; 1,805,264; 3,309,771; 3,535,787; and 3,990,150. Of these, the most significant is U.S. Pat. No. 1,299,364 which shows a partial dental bridge having wire or hard metal anchors embedded therein, and extending in the form of a vertically oriented loop with both of its ends fixed to the bridge. An abutment is attached to a natural tooth, and a keeper in the form of a hard metal plate is soldered to the abutment.

The keeper is formed with grooves in its side and top, to receive the anchor loop, which is arranged to snap around the generally rectangular extent (in cross-section) of the groove. Thus any pivoting of the bridge along an axis transverse to the attachment must overcome the stiffness of the hard wire at the base ends of the loop; and any rotational motion of the loop around the groove must overcome (and tend to weaken) the clasping action of the wire loop against the sides of the groove in the keeper. Thus, stresses due to flexing lengthwise of the jaw tend to misalign the attachment loop and bend or work the wire, while torque tending to rotate the loop will tend to transmit into the keeper.

SUMMARY OF THE INVENTION

The present invention provides a novel attachment arrangement whereby a partial denture, either single or double sided, may be attached to abutting teeth of the wearer by constructing for the abutting teeth crowns which are built in conventional manner, but which are provided with a special anchor member. These crowns are attached to a natural tooth in the conventional way, for example by cementing. The partial denture is provided with a clip which is included in the denture, and which easily by firmly clasps to the anchor member formed in the crown of the abutting tooth. The anchor/clip attachment is appropriately relieved once it is constructed for the particular patient, such that the partial denture has adequate flexibility in use, without transmitting much stress to the crown. Also, the anchor/clip interface is essentially that of mating cylindrical surfaces, and the clip will tend to rotate on the anchor surface rather than transmit torque to the crown.

Thus, the denture can seat upon the gum of the wearer as it is intended and designed to do without transferring stress through the anchor/clip attachment to the abutting or anchoring teeth. Furthermore, the present invention provides a novel process of constructing a partial denture to include such attachment, whereby the anchor member and the clip of the denture are precisely aligned to assure an accurate fit of the denture each time it is placed in the wearer's mouth.

In particular, the novel process and the extra coronal attachment mechanism provided by this invention includes an anchor member which is cast into, or as part of, the crown being built for the abutting or attaching tooth. Thus, as the crowns are built on the master cast of the mouth, the anchor member (or a mold for it), preferably in the form of a grooved cylinder, is precisely located by means of a suitable mandrel, and incorporated into the pattern for the crown, after which the crown is cast in the usual way. The crown with the integral anchor member is then seated on the master cast and the partial denture is built up from this point. The region on the cast corresponding to that region of the patient's mouth where the attachment will be located is appropriately blocked off, for example by constructing a waxed area of appropriate size and shape, using blocks or parts provided for this purpose. Then construction of the partial denture proceeds in conventional fashion, incorporating the attachment clip, or a socket for mounting the clip.

The framework of the partial denture is thus located with respect to the attachment, the clips being attached to the anchor members during this time, and the appropriate sockets (where used) for receiving the clips on the frame of the partial denture being appropriately aligned, such that after the partial denture is constructed, removal of the clips from the anchors on the crowns, and attachment of the clips to the completed partial denture in the case of replaceable clips, results in a finished attachment ready for fitting of the mouth of the wearer. The attachment between the clip and the anchor member is preferably in the form of a horse-shoe shaped clip which snaps around a relieved or undercut section of the cylindrical anchor member, such that the clip can snap endwise, from above or below as the case may be, onto and around the groove in the anchor member, thereby locating the partial denture both lengthwise and crosswise. A surface of the anchor member farthest from the gum preferably is cut away slightly, to relieve the connection between the clip and the anchor member to the extent of permitting a slight rocking motion of the base of the clip, where it is attached to the denture, in a direction generally transverse to the jaw line and the axis of the cylindrical anchor member. This allows for flexure of the clip, especially in a downward-rearward direction, on the anchor member without subjecting the anchor member, and thus the crown on which it is formed, to stress as force is exerted against the partial denture at a location remote, usually rearward, from the attachment point.

In one form the removable clips are provided with a threaded shank in their base, and these shanks extend through an appropriate hole formed in the socket in the frame of the partial denture, and may be held in place by suitable locking nuts or the like, as a result of which the clips can be easily and quickly replaced if the clips should be bent or broken at any time. In another embodiment the clip is fitted into, but removable from, the socket which is cast into the denture frame.

The primary object of the present invention therefore is to provide a novel attachment for a partial denture, commonly referred to as an extra coronal attachment, and a process of constructing the same, whereby the partial denture is easily attached and detached by means of clips to one or more anchor members formed on crowns which are constructed on the abutting or anchoring teeth of the wearer and attached thereto in conventional fashion, and wherein the clip/anchor connection essentially isolates the crowns from flexure or torsional forces due to movements of the denture; to provide such an attachment which is adaptable for attaching partial dentures either to one or both sides of the wearer's mouth; to provide such an attachment and process which is quickly constructed using conventional tools and techniques, with the exception of a few parts that are readily available in kit form to the dental laboratory.

Other objects and advantages will be apparent from the following description, the accompanying drawings and the appended claims.

BRIEF DESCRIPTION OF THE DRAWINGS

FIG. 1 is a perspective view showing the alignment of the anchor member of the attachment to the mold from which a crown is made;

FIG. 2 is an enlarged perspective view showing the anchor member waxed up to the crown mold;

FIG. 3 illustrates the crown, having been molded and with the anchor member now an integral part, positioned on the master cast, with the attachment clip for the denture located above the anchor member;

FIG. 4 is a view showing the manner in which the clip and socket are positioned on the master cast for proper alignment in the construction of the resulting denture;

FIG. 5 is a perspective view showing the skeleton or frame of the partial denture, with the clips positioned on the anchor members of the crowns, and illustrating the manner in which the clips are attached to the frame prior to construction of the artificial dentures thereon;

FIG. 6 is a perspective view of one of the crowns with the integral anchor member showing the relief to the anchor member which allows flexing of the completed denture in use;

FIG. 7 illustrates the application of the invention to a bar type prosthesis;

FIG. 8 shows another form of socket pattern;

FIG. 9 shows the pattern of FIG. 8 located over the anchor member on a master cast;

FIG. 10 shows the manner of using the socket pattern in waxing up;

FIG. 11 shows the anchor attachment pattern of this form;

FIG. 12 shows the anchor attachment pattern in place for completing the internal configuration of the socket;

FIG. 13 is a view of the attachment clip which is applied to the finished socket; and FIG. 14 is a cross-sectional view of the modified clip on the anchor member.

DESCRIPTION OF THE PREFERRED EMBODIMENT

Referring to FIGS. 1 and 2, there is shown a master cast 10 of a patient's lower jaw, from which the molars have been removed, and on which the bicuspids are being repaired by conventional crowns (shown as patterns 12) constructed in the conventional way, to be cemented in place over the properly formed base of the natural tooth, indicated by the dotted outline 13. The outline is shown only on the left side for purposes of simplification; however, it will be understood that a crown is constructed for two of these anchoring or abutting teeth to form the necessary support for the artificial denture on both sides of the wearer's mouth. The waxed up pattern 12 of the crown is formed in the conventional way on the member 13, which is a part of the master cast, and as part of forming the crown pattern a cylindrical metal anchor member 15 is located in a precise position, and at a precise angle with respect to the master cast, by holding the anchor member 15 in a mandrel 17. This angle places the longitudinal centerline of the anchor member in a position extending rearward and downward over the jaw line.

The anchor member is then attached to the crown pattern 12 by an appropriate shaped mass of wax or the like, shown generally in FIG. 2 by the reference numeral 18. It should be noted in FIG. 1 that the end of the anchor member around which the temporary holding wax is applied includes one or more cylindrical grooves or the like, indicated generally at 19, and the other end of the anchor member is provided with a precisely undercut cylindrical groove 20. The groove 20 is engaged by a horseshoe shape retainer 22 at the end of mandrel 17, thereby locating the anchor member exactly in position, and at the correct angle, during this operation. The crown pattern 12 with the anchor member attached, is then removed from the master cast and the actual crown is cast, using known techniques. If the anchor member 15 is of a material compatible with the crown, the anchor member can be cast into the crown. Alternatively, the member 15 can be a suitable pattern, as of polypropylene or an acrylic (e.g. Lucite), and the entire crown and anchor cast together.

The crown itself is shown in FIG. 3 at 25, with the anchor member now integral with the crown, projecting at the proper angle therefrom, and with the cylindrical groove or anchor surface 20 exposed. This crown/anchor member combination is therefore adapted to provide the precise attachment point for the partial denture, and the attachment to the anchor member is made by a horseshoe shaped clip 28, shown separated from the anchor member in FIG. 3, and apart from the partial denture.

The clip includes a pair of downwardly extending arms 29 which are shaped to surround the anchor member, fitting within the groove 20 and tightly engaging the surfaces of that groove. The base section 30 of the clip is generally rectangular in cross-section, in the preferred embodiment, and extending upwardly from it is a threaded attachment stud 32. The clip is snapped onto the anchor member with the crown 25 in the master cast, and the region surrounding the attachment is then prepared for blocking up, as part of the subsequent construction of the partial denture.

For this purpose a small box or socket 35 is provided having an aperture 36 which is sized to fit closely around the shank 32 of the clip. The box is placed around the clip and the anchor member, with the shank extending through the hole 36, and the interior of the box is filled with wax. The sides of the box are then cut, for example by forming dovetailed or grooved slots therein, and the lower edges of the box are trimmed as necessary to fit to the region of the gum line of the master cast. The purpose of this is that the box (one on each side) eventually becomes cast into the framework of the partial denture, thus providing an accurate socket to engage the denture with the clip 28 when finally assembled.

The dovetails are indicated generally at 38 in the sides of the box 35, and their purpose is to provide a secure joint between the box and the framework of the denture which is next formed. This is done in conventional fashion, by making a mold of the master cast, and withdrawing the mold therefrom, taking the boxes 35 into the mold. In some instances it is desirable to provide small balls of sticky wax on the outer surfaces of the boxes, to assure that they remove cleanly from the master cast into the mold. The framework for the denture is then molded, in conventional manner, using the thus formed mold with the boxes therein, and the cast framework thereby incorporates the boxes.

Such framework is shown by the general reference numeral 40 in FIG. 5. The boxes trimmed and incorporated as sockets into the framework, are shown in alignment with the clips 28. Each clip, however, is illustrated removed from the framework, but aligned therewith as shown by the dot-dash center lines, and attached to the anchor member on the crowns 25 and 25a which are, at this time, fitted onto the master cast. Above the denture framework 40 there are shown the retainer nuts 42 which are provided to thread onto the studs 32 of the clips, thereby retaining the clips to the framework, securely seated such that they will not twist or move out of alignment with the framework.

Next, the artificial dentures are built on the frame 40, in known manner, preferably leaving the frame attached to the master cast for the best alignment. Then, once the partial denture is completed and removed, the ends of the anchor members are provided with a tapered cut across their upper portion, as shown in FIG. 6, this cut preferably extending at approximately forty-five degrees to the longitudinal center line of the cylindrical members, and being deep enough that a portion of the top of the slot 20 is removed. This cut is illustrated in FIG. 6 by the general reference numeral 45. The purpose is to permit a small amount of rocking action of the clip 28 within the tops of the slots when the wearer of the partial denture exerts pressure against the molars, rearward of the attachment connection. This enables sufficient flexure of the denture that it will seat securely on the gums, but will not transmit appreciable twisting force through the attachment connection to the abutting crowns 25 and 25a which form the ultimate support of the denture to the mouth of the wearer.

Furthermore, the cylindrical surface interface between the clip and the anchor surface (groove 20) allows for rotational movement in the attachment. This is desirable since the wearer might bite hard on one side, thereby producing a torque at the attachment points. The accommodation of rotation at the attachment interface effectively isolates the crowns from this torque.

FIG. 7 shows a modification of the invention applied to a bar-type prosthesis, for example where a partial denture is to be constructed to fill a space between two teeth on the same side of the mouth. Here a first crown 50 and a second crown 52 are constructed in conventional fashion by building them up on the master cast and then casting the crowns from the wax. The anchor member 55 is provided as a bar of suitable length having gripping grooves, or the like (not shown) near its ends, and which is waxed up the crown patterns on the cast, and then formed as an integral part of both crowns, joining them and bridging the space between them. The anchor member is also provided with a cylindrical recess 56 sized to receive the clip of the partial denture in the same manner as previously described. Thus, the framework and the attachment for this partial denture is built in the same way, and is clipped to the anchor bar 55, in the same fashion as previously described.

FIGS. 8-14 illustrate another embodiment of the invention. The parts shown in FIG. 8, FIG. 11 and FIG. 13 can be molded of a suitable plastic material such as polypropylene, and can be provided in a kit along with a plastic anchor-forming cylinder 15. The block shown in FIG. 8 has a generally rectangular outer dimension as shown at 60, and it is provided with a part cylindrical passage 62 into which is molded a rib or ring 64. The block 60 is adapted to snap onto the anchor formed integrally with the crown, with the rib 64 entering the anchor surface or groove 20, as shown generally in FIGS. 9 and 10. In FIG. 9 the part is in position to be snapped onto the anchor, and in FIG. 10 the part is shown snapped into position with wax applied at 65 around the base of the part 60.

The standard procedure for building up the bridgework then is followed, and the part 60 acts to mold an appropriate rectangular socket into the bridgework, as shown generally in FIG. 12. At this point the part 60 may be disposed of, and a part as shown in FIG. 11 is used to fit the bridgework to the master cast and the anchors formed on the crowns as shown in FIG. 12.

Referring to FIG. 11, the part 70 is similar in appearance to the part 60, having an internal cylindrical opening 72 and a rib 74, however, the top of this part is relieved at the upper edges, as indicated at 75, and beneath each relieved upper edge there is a slot 77. Also, the transverse outer dimension of the part 70 is slightly undersized with respect to the part 60, so that the part 70 slips tightly into the sockets in the denture.

With the part 70 fitted into the sockets, or alternatively fitted onto the anchors, a quantity of a self-curing polymeric material is applied between the socket and the part 70, and the denture is pressed tightly onto the parts 70 while in place on the anchors. As the material cures, it forms a pair of opposed ridges along the upper interior sides of the socket, these being shown generally at 78 in FIG. 14.

With the denture removed from the master cast, after the material is cured, the parts 70 are then carefully pried from the sockets, and the final clip 80, as shown in FIG. 13, is snapped into the socket. This clip has the same longitudinal cylindrical opening 82 and internal rib 84. It is provided with a head 85 shaped generally to the configuration of the top of the part 70, and recesses 87 provided to engage over the ribs 78 in the socket, locking the clip in place. The outer walls of the clip 80 are curved at both upper and lower sides, providing sufficient relief that the head 85 can snap into place, and also providing clearance as shown at 88 in FIG. 14. This allows the lower sides of the clip to flex sufficiently in the socket as the denture is applied and removed from the anchors during normal use.

While the process and forms of apparatus herein described constitute preferred embodiments of this invention, it is to be understood that the invention is not limited to this precise process and forms of apparatus, and that changes may be made therein without departing from the scope of the invention.

What is claimed is:

1. An extra coronal attachment comprising
   a cylindrical anchor member formed as part of a crown adapted to be fitted to a natural tooth and having an axis extending in predetermined angular relation over the jaw line;
   a cylindrical anchor surface formed concentrically in said anchor member and of a different diameter than said member;
   and a clip adapted for inclusion in a partial denture
      said clip having an elongated semi-cylindrical interior cavity with an opening extending the length thereof and constructed to fit closely over said anchor member, and
      rib means formed in the interior of said cavity concentrically therewith and arranged to interfit with said anchor surface allowing rotational movement of said clip around said axis when said clip is attached to said anchor member and resisting movement of said clip along said anchor member in a direction parallel to said axis,
      said clip being sufficiently flexible along the sides of said opening to be forced onto and off of said anchor member from a side thereof,
   whereby said clip can flex partially in a direction transverse to said axis in response to stress forces transmitted in the form of a rocking action of the denture, the rotation and flexing of said clip thereby relieving said anchor member from twisting forces.

2. A device as defined in claim 1, wherein said clip is constructed of a material less wear resistant than said anchor member, and said clip is removable from said socket.

3. The process of constructing an extra coronal attachment for a partial denture, comprising the steps of
   (a) building crowns on two spaced apart natural teeth,
   (b) casting a cylindrical anchor member into each of said crowns, each said anchor member having a longitudinal axis extending along the jaw at a predetermined angle and having a concentric cylindrical anchor surface of different diameter from said member,
   (c) building the partial denture and constructing socket members integral with the denture using blocks of predetermined shape attached to the anchor surfaces as the framework of the denture is built up around the blocks and referenced to the crowns,
   attaching anchoring clips as a replaceable part in said socket, said clip having a cylindrical cavity designed to engage substantially around the anchor surface and having a rib member dimensioned to interfit with said anchor surface to permit rotational movement between the clips and the anchor members and to resist longitudinal movement of the clips on the anchor members.

* * * * *